(12) United States Patent
Wang et al.

(10) Patent No.: US 12,076,140 B2
(45) Date of Patent: Sep. 3, 2024

(54) OXIMETRY PROBE AND METHOD OF OPERATING THE SAME, AND OXIMETRY SENSOR

(71) Applicant: SOLARIS MEDICAL TECHNOLOGY, INC., Guangdong (CN)

(72) Inventors: Ganbing Wang, Guangdong (CN); Chunhui Xu, Guangdong (CN)

(73) Assignee: SOLARIS MEDICAL TECHNOLOGY, INC., Shenzhen (CN)

( * ) Notice: Subject to any disclaimer, the term of this patent is extended or adjusted under 35 U.S.C. 154(b) by 928 days.

(21) Appl. No.: 17/027,635

(22) Filed: Sep. 21, 2020

(65) Prior Publication Data
US 2021/0000398 A1 Jan. 7, 2021

Related U.S. Application Data

(63) Continuation-in-part of application No. PCT/CN2019/078947, filed on Mar. 21, 2019.

(30) Foreign Application Priority Data
Mar. 21, 2018 (CN) .......................... 201810235474.2

(51) Int. Cl.
*A61B 5/1455* (2006.01)
*A61B 5/00* (2006.01)

(52) U.S. Cl.
CPC ........ *A61B 5/14552* (2013.01); *A61B 5/6826* (2013.01); *A61B 5/6838* (2013.01)

(58) Field of Classification Search
CPC .............. A61B 5/1455; A61B 5/14552; A61B 2562/22; A61B 2562/222
See application file for complete search history.

(56) References Cited

U.S. PATENT DOCUMENTS 5,818,985 A * 10/1998 Merchant ........... A61B 5/14551
600/310
5,995,855 A * 11/1999 Kiani ................. A61B 5/14552
600/323

(Continued)

FOREIGN PATENT DOCUMENTS

CN 101080192 A 11/2007
CN 102670211 A 9/2012
(Continued)

*Primary Examiner* — Eric F Winakur (57) ABSTRACT

An oximetry probe and an operating method thereof, and an oximetry sensor. The oximetry probe includes an oximetry sensor which includes a detection end and an output end, and an adapter. The detection end includes a photodetector and multiple light-emitting elements connected in series. The output end has multiple output ports. Adjacent output ports are electrically connected to two sides of the corresponding light-emitting element. The adapter has a first adapter end and a second adapter end between which multiple wires are provided. The first adapter end is electrically connected with an input end of the monitor. When the second adapter end is connected to the output end, the wires are electrically connected with the output ports to form closed circuit to enable the light-emitting element to emit light which is received by the photodetector to generate a signal involving blood oxygen saturation to be displayed on the monitor.

19 Claims, 4 Drawing Sheets

(56) References Cited

U.S. PATENT DOCUMENTS 6,697,656 B1 * 2/2004 Al-Ali ................ A61B 5/14552
600/323
2010/0081945 A1 4/2010 Sethi et al.

FOREIGN PATENT DOCUMENTS

| CN | 103271745 A | 9/2013 |
| CN | 104853672 A | 8/2015 |

* cited by examiner

OXIMETRY PROBE AND METHOD OF OPERATING THE SAME, AND OXIMETRY SENSOR

CROSS-REFERENCE TO RELATED APPLICATIONS

This application is a continuation of International Patent Application No. PCT/CN2019/078947, filed on Mar. 21, 2019, which claims the benefit of priority from Chinese Patent Application No. 201810235474.2 with a filing date of Mar. 21, 2018. The content of the aforementioned applications, including any intervening amendments thereto, is incorporated herein by reference in their entirety.

TECHNICAL FIELD

The present application relates to medical monitoring equipment, and more particularly to an oximetry probe and a method of operating the same, and an oximetry sensor.

BACKGROUND

The monitor manufacturers vary in the oximetry technique, which renders their corresponding pulse oximetry sensors technically different from each other, so that a sensor produced by one manufacturer generally cannot be compatible with a monitor produced by another manufacturer.

However, actually, the monitors used in different departments are often produced by different manufacturers. For example, there may be four kinds of monitors used in the four clinical environments that a patient may undergo in one treatment course, that is, monitor A is used in the operating room; monitor B is used in the postanesthesia care unit; monitor C is used in the intensive care unit (ICU); and monitor D is used in the general ward, which indicates that four kinds of pulse oximetry sensors are required to be prepared to satisfy the clinical requirements during the same treatment course.

Considering the above, since different monitors generally have different ports, it is necessary to use four kinds of pulse oximetry sensors respectively compatible with the four different monitors in the same treatment course, which brings an increase not only in the clinical workload and operation complexity, but also in the treatment cost.

SUMMARY

An object of this application is to provide an oximetry probe and an oximetry sensor used therein to overcome the defects in the prior art that it is required to correspondingly replace the oximetry sensor to ensure the compatibility in terms of signal when the monitor is changed.

Technical solutions of the present application are described as follows.

In a first aspect, this application provides an oximetry probe, comprising:
an oximetry sensor; and
an adapter;
wherein the oximetry sensor comprises a detection end and an output end; the detection end comprises a photodetector and a plurality of light emitting elements capable of independently emitting light beams of different peak wavelengths; the light emitting elements are connected in series; the output end has a plurality of output ports; two adjacent output ports are electrically connected to two sides of the corresponding light emitting element, respectively;

the adapter has a first adapter end and a second adapter end; the first adapter end is configured to adapt to an input end of a target monitor; the second adapter end is configured to adapt to the output end of the oximetry sensor; a plurality of first wires are provided between the second adapter end and the first adapter end; the first adapter end is electrically connected with the input end of the target monitor to allow one end of each first wire to be electrically connected with a corresponding input port of the input end of the target monitor; the output ports are greater than the first wires in number; when the second adapter end is connected to the output end, the other end of each first wire is electrically connected with the corresponding output port to form a closed circuit, so as to enable the light emitting element between the two adjacent output ports in the closed circuit to emit light, and the emitted light is received by the photodetector to generate a detection signal associated with a blood oxygen saturation of a patient which is displayed on the target monitor.

In an embodiment, there are N light emitting elements, and N is greater than or equal to 3; the N light emitting elements are connected in series; N+1 connection ports are provided at the detection end; the two adjacent connection ports are located at two sides of the corresponding light emitting element, respectively; the output end has N+1 output ports in one-to-one correspondence to the connection ports; and each connection port is electrically connected with the corresponding output port.

In an embodiment, the oximetry sensor further comprises a cable; the cable has N+1 second wires; and the second wires connect each connection port with the corresponding output port, respectively.

In an embodiment, the first wires are the same as input ports of the target monitor in number; the first adapter end has a plurality of first adapter ports; and the first adapter ports are the same as the first wires in number.

In an embodiment, the second adapter end of the adapter has a plurality of second adapter ports, wherein the second adapter ports are the same as the output ports in number.

In an embodiment, the first adapter end is configured to connect with the input end of the target monitor or to connect with an external adapter connected to the input end of the target monitor.

In an embodiment, the light emitting elements comprise at least two red light emitting tubes and at least one infrared light emitting tube; the at least two red light emitting tubes are connected in series to form a first series circuit; the at least one infrared light emitting tube is connected in series to form a second series circuit; the first series circuit is connected in series with the second series circuit; or the light emitting elements comprise at least one red light emitting tube and at least two infrared light emitting tubes; the at least one red light emitting tube is connected in series to form a first series circuit; the at least two infrared light emitting tubes are connected in series to form a second series circuit; the first series circuit is connected in series with the second series circuit.

In an embodiment, the detection end further comprises a circuit board; and
the at least two red light emitting tubes and the at least one infrared light emitting tube are welded to the circuit board; or
the at least one red light emitting tube and the at least two infrared light emitting tubes are welded to the circuit board.

In an embodiment, the detection end further comprises a first circuit board and a second circuit board; and the at least two red light emitting tubes are welded to the first circuit board and the at least one infrared light emitting tube is welded to the second circuit board; or the at least one red light emitting tube is welded to the first circuit board and the at least two infrared light emitting tubes are welded to the second circuit board.

In an embodiment, the detection end further comprises at least two first circuit boards and at least one second circuit board; the at least two red light emitting tubes are welded to the at least two first circuit boards in one-to-one correspondence; the at least one infrared light emitting tube is welded to the at least one second circuit board in one-to-one correspondence; or the detection end further comprises at least one first circuit board and at least two second circuit boards; the at least one red light emitting tube is welded to the at least one first circuit board in one-to-one correspondence; the at least two infrared light emitting tubes are welded to the at least two second circuit boards in one-to-one correspondence.

In an embodiment, the light emitting elements are light emitting diode (LED) lights.

Compared to the prior art, the oximetry probe has the following beneficial effects.

In the oximetry probe of the invention, a plurality of wires are provided in the adapter in advance. One end of the wires is plugged into the input ports of the corresponding monitor at the first adaptation end of the adapter to enable the adaptation to the monitor through electrical connection. Then the output end of the sensor is connected with the second adaptation end of the adapter to enable the other end of the wires to be electrically connected with the corresponding output ports of the sensor, so as to selectively connect part of the light emitting elements at the detection end to form a closed circuit. The light with specified peak wavelength which is emitted by these electrically-connected light emitting elements can be recognized by the monitor, achieving the adaptation of the sensor to the monitor. Moreover, considering the provision of multiple light emitting elements capable of independently emitting light at the detection end, it is possible to selectively control the light emission of each light emitting element as required, exciting the light combination corresponding to the specific monitor and achieving the adaptation to different monitors. Given the above, the probe of the invention has wide adaptation range and simple operation. When it is required to use a different monitor, it is only required to disconnect the output end of the sensor from the second adaptation end of the adapter and then connect the output end of the sensor to a second adaptation end of an adapter adapting to the different monitor without the need to repeatedly remove and place the detection end of the sensor, simplifying the operation and lowering the cost.

In a second aspect, this application provides an oximetry sensor, comprising:

a detection end; and an output end;

wherein the detection end comprises a photodetector and a plurality of light emitting elements capable of independently emitting light beams of different peak wavelengths; the light emitting elements are connected in series; the output end has a plurality of output ports; two adjacent output ports are electrically connected to two sides of the corresponding light emitting element, respectively; and the output ports are configured for electrical connection with an adapter adapting to a monitor.

In an embodiment, there are N light emitting elements, and N is greater than or equal to 3; the N light emitting elements are connected in series; N+1 connection ports are provided at the detection end; the two adjacent connection ports are located at two sides of the corresponding light emitting element, respectively; the output end has N+1 output ports in one-to-one correspondence to the connection ports; and each connection port is electrically connected with the corresponding output port.

In an embodiment, the oximetry sensor further comprises:

a cable;

wherein the cable has N+1 wires; and the wires connect each connection port with the corresponding output port, respectively.

In an embodiment, the light emitting elements comprise at least two red light emitting tubes and at least one infrared light emitting tube; the at least two red light emitting tubes are connected in series to form a first series circuit; the at least one infrared light emitting tube is connected in series to form a second series circuit; the first series circuit is connected in series with the second series circuit; or the light emitting elements comprise at least one red light emitting tube and at least two infrared light emitting tubes; the at least one red light emitting tube is connected in series to form a first series circuit; the at least two infrared light emitting tubes are connected in series to form a second series circuit; the first series circuit is connected in series with the second series circuit.

In an embodiment, the detection end further comprises a circuit board; and the at least two red light emitting tubes and the at least one infrared light emitting tube are welded to the circuit board; or the at least one red light emitting tube and the at least two infrared light emitting tubes are welded to the circuit board.

In an embodiment, the detection end further comprises a first circuit board and a second circuit board; and the at least two red light emitting tubes are welded to the first circuit board and the at least one infrared light emitting tube is welded to the second circuit board; or the at least one red light emitting tube is welded to the first circuit board and the at least two infrared light emitting tubes are welded to the second circuit board.

In an embodiment, the detection end further comprises at least two first circuit boards and at least one second circuit board; the at least two red light emitting tubes are welded to the at least two first circuit boards in one-to-one correspondence; the at least one infrared light emitting tube is welded to the at least one second circuit board in one-to-one correspondence; or the detection end further comprises at least one first circuit board and at least two second circuit boards; the at least one red light emitting tube is welded to the at least one first circuit board in one-to-one correspondence; the at least two infrared light emitting tubes are welded to the at least two second circuit boards in one-to-one correspondence.

In an embodiment, the light emitting elements are light emitting diode (LED) lights.

Compared to the prior art, the oximetry sensor of the invention has the following beneficial effects.

In the oximetry sensor provided herein, considering the provision of multiple light emitting elements capable of independently emitting light at the detection end, it is possible to selectively control the light emission of each light emitting element as required, exciting the light combination corresponding to the specific monitor to achieve the adaptation to different monitors. Given the above, the sensor of the invention has desirable adaptation range and simple operation. When it is required to use a different monitor, it is only required to disconnect the output end of the sensor from the second adaptation end of the adapter and then connect the output end of the sensor to a second adaptation end of an adapter adapting to the different monitor without the need to repeatedly remove and place the detection end of the sensor, simplifying the operation and reducing the consumption of medical supplies.

In a third aspect, this application also provides a method of operating the above oximetry probe, comprising:
(1) connecting the first adapter end to the target monitor to allow one end of each first wire to be electrically connected with the corresponding input port of the target monitor;
(2) connecting the second adapter end with the output end to allow the other end of each first wire to be electrically connected with the corresponding output port to form a closed circuit to enable the light emitting element between the two adjacent output ports in the closed circuit to emit light;
(3) receiving, by the photodetector, the emitted light to generate a detection signal associated with a blood oxygen saturation of a patient; and displaying the detection signal on the target monitor;
(4) when it is required to replace the target monitor with another monitor for blood oxygen monitoring, disconnecting the output end from the second adapter end; and
(5) connecting the output end to a second adapter end of another adapter connected with the another monitor to enable the electrical connection of the corresponding light emitting element; receiving, by the photodetector, the light emitted from the corresponding light emitting element to generate a detection signal associated with the blood oxygen saturation of the patient; and displaying the detection signal on the another monitor.

Compared to the prior art, the operating method of the oximetry probe provided herein has the following beneficial effects.

In the operating method, an adapter adapting to the target monitor is connected to the target monitor in advance, and then a second adapter end of the adapter is connected to the output end of the sensor to selectively connect specific light emitting elements from which the emitted light can be recognized by the target monitor, achieving the adaptation of the sensor to the monitor. Therefore, when it is required to use a different monitor, it is only required to disconnect the output end of the sensor from the second adapter end of the adapter and then connect the output end of the sensor to a second adapter end of an adapter adapting to the different monitor without the need to repeatedly remove and place the detection end of the sensor, simplifying the operation and reducing the workload of the medical staff and the consumption of medical supplies.

BRIEF DESCRIPTION OF THE DRAWINGS

The technical solutions of the invention will be described more clearly and completely below with reference to the accompanying drawings and the embodiments. Obviously, illustrated in the drawings are merely some embodiments of the invention, and those skilled in the art can obtain other drawings based on the drawings provided herein without sparing any creative effort, which should still fall within the scope of the invention.

In the drawings, 10—oximetry sensor; 11—detection end; 12—output end; 13—first cable; 111—light emitting element; 112—connection point; 121—output port; 131—second wire; 20—adapter; 21—first adapter end; 22—second adapter end; 23—second cable; 211—first adapter port; 221—second adapter port; 231—first wire; and 30—monitor.

DETAILED DESCRIPTION OF EMBODIMENTS

The embodiments of the invention will be described in detail below with reference to the drawings. In the drawings, the same or similar reference numerals indicate the same or similar elements or the elements with the same or similar functions. These embodiments are merely illustrative of the invention, and are not intended to limit the invention.

It should be understood that as used herein, the orientation or positional relationship indicated by terms "length", "width", "upper", "lower", "front", "rear", "left", "right", "vertical", "horizontal", "top", "bottom", "inner" and "outer" is in accordance with the orientation or positional relationship shown in the drawings. These terms are merely for the convenience of describing the present invention, and are not intended to indicate or imply that the device or element must be placed in a specific orientation or configured and operated in a specific orientation, and thus they should not be understood as limitations to the invention.

As used herein, terms "first" and "second" are merely illustrative and are not intended to indicate or imply relative importance or the number of the corresponding technical features. Thus, the terms "first" and "second" may explicitly or implicitly indicate the inclusion of one or more of the corresponding features. Unless otherwise specified, the phrase "a plurality of" means that there are two or more corresponding features.

Unless otherwise specified, terms "install", "link", "connect" and "fix" should be understood in a broad sense. For example, these terms may refer to fixed connection, detachable connection or integrated formation; mechanical connection or electrical connection; direct connection or indirect connection through an intermediate medium; the internal communication of two components or the interaction between two components. Those skilled in the art can understand the specific meaning of the above terms in the present invention according to the specific situation.

Figure 1:
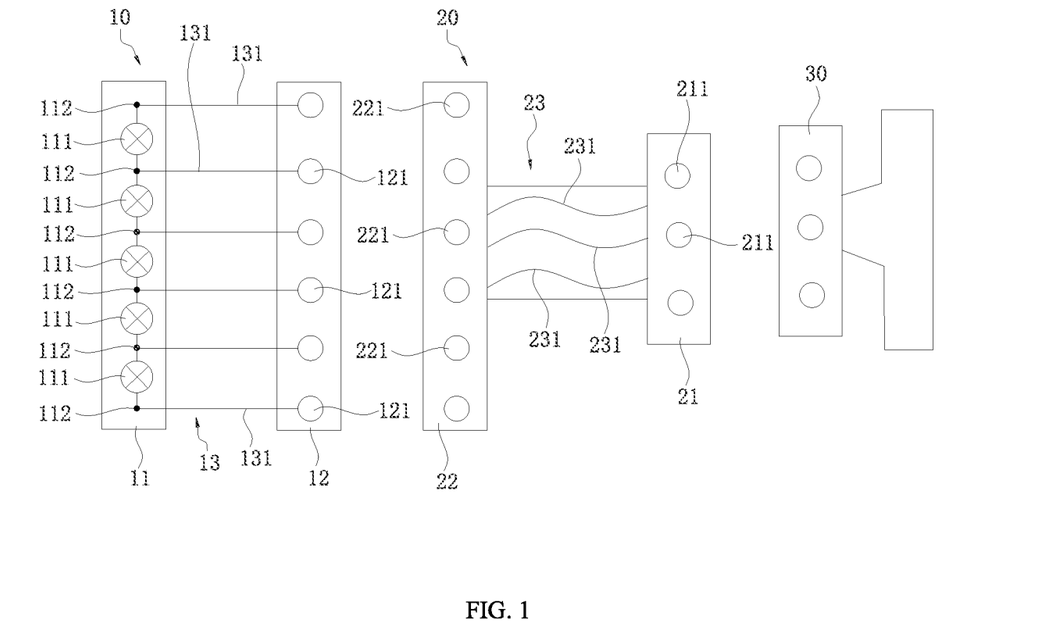
FIG. 1 schematically illustrates an operation principle of an oximetry probe according to an embodiment of the present invention.
Figure 2:
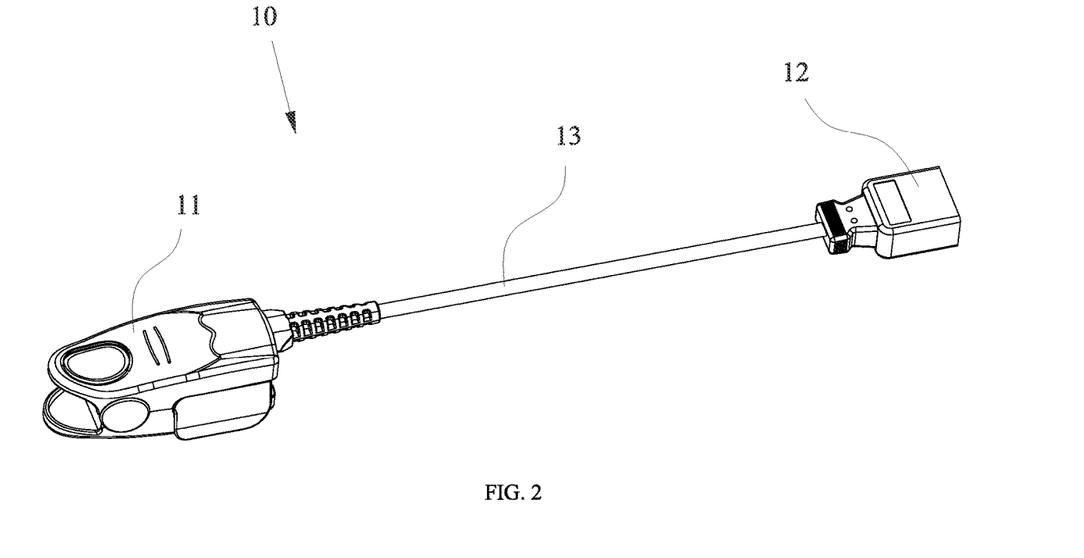
FIG. 2 schematically depicts a structure of an oximetry sensor according to an embodiment of the present invention.
Figure 3:
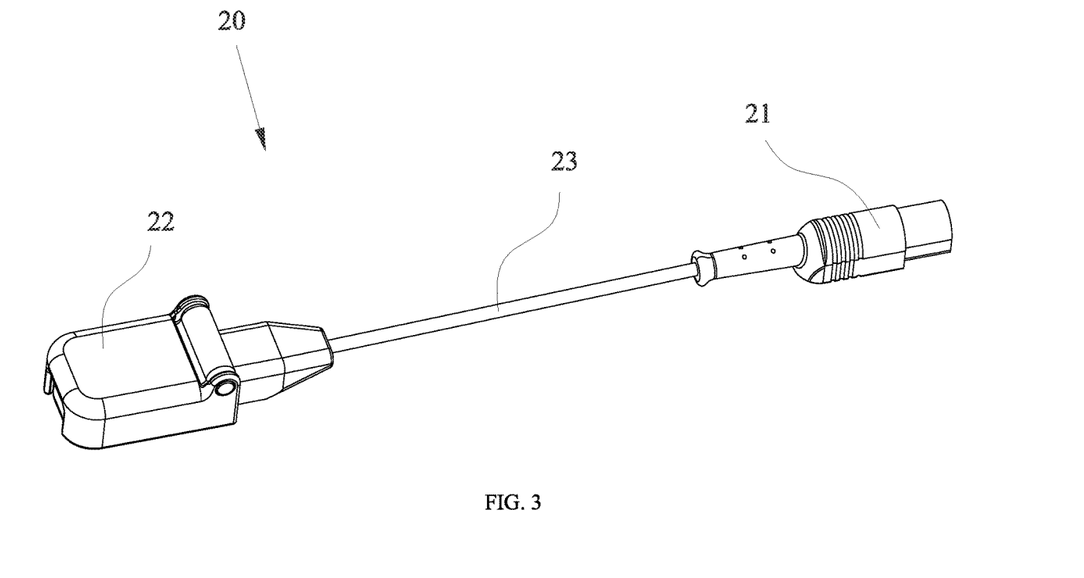
FIG. 3 schematically depicts a structure of an adapter according to an embodiment of the present invention.

As shown in FIGS. 1-3, this application provides an oximetry probe, which includes an oximetry sensor 10 and an adapter 20.

The oximetry sensor 10 includes a detection end 11 and an output end 12. The detection end (11) includes a photodetector and a plurality of light emitting elements 111 capable of independently emitting light beams of different peak wavelengths. The light emitting elements 111 are connected in series. The output end 12 has a plurality of output ports 121. Two adjacent output ports 121 are electrically connected to two sides of the corresponding light emitting element 111, respectively.

The adapter 20 has a first adapter end 21 and a second adapter end 22, where the first adapter end 21 is configured to adapt to an input end of a target monitor 30; and the second adapter end 22 is configured to adapt to the output end 12. A plurality of first wires 231 are provided between the second adapter end 22 and the first adapter end 21. The first adapter end 21 is electrically connected with the input end of the target monitor 30 to allow one end of each first wire 231 to be electrically connected with the corresponding input port of the target monitor 30. The output ports 121 are greater than the first wires in number 231. When the second adapter end 22 is connected to the output end 12, the other ends of the first wires 231 are electrically connected with the corresponding output ports 121, respectively, to form a closed circuit, so as to enable the light emitting element 111 between the two adjacent output ports 121 in the closed circuit to emit light, and the emitted light is received by the photodetector to generate a detection signal associated with a blood oxygen saturation of a patient which is displayed on the target monitor 30.

Due to the provision of the plurality of first wires 231 in the adapter 20 in advance, when one end of the each first wire 231 is plugged into the corresponding input port of the target monitor 30 at the first adapter end 21, the adapter 20 is electrically connected with the monitor 30, achieving the adaptation to the monitor 30. Then the output end 12 is connected with the second adapter end 22 to enable the other end of each first wire 231 to be electrically connected with the corresponding output port 121, so as to selectively connect part of the light emitting elements 111 at the detection end 11 to form a closed circuit. The light with specified peak wavelength which is emitted by these electrically-connected light emitting elements 111 can be recognized by the monitor 30, achieving the adaptation of the oximetry sensor 10 to the monitor 30. Moreover, considering the provision of multiple light emitting elements 111 capable of independently emitting light at the detection end 11, it is possible to selectively control the light emission of each light emitting element 111 as required, exciting the light combination corresponding to the specific monitor 30 to achieve the adaptation to different monitors 30. Given the above, the oximetry probe of the invention has wide adaptation range and simple operation. When it is required to use a different monitor 30, it is only required to disconnect the output end 12 of the oximetry sensor 10 from the second adapter end 22 of the adapter 20 and then connect the output end 12 of the oximetry sensor 10 to a second adapter end 22 of an adapter 20 adapting to the different monitor without the need to repeatedly remove and place the detection end 11 of the oximetry sensor 10, simplifying the operation and reducing the consumption of medical supplies.

In an embodiment illustrated in FIG. 1, there are N light emitting elements 111, and N is greater than or equal to 3. The N light emitting elements 111 are connected in series. N+1 connection ports 112 are provided at the detection end 11. The two adjacent connection ports 112 are located at two sides of the corresponding light emitting element 111, respectively. The output end 12 has N+1 output ports 121 in one-to-one correspondence to the connection ports 112. Each connection port 112 is electrically connected with the corresponding output port 121. Specifically, when the output end 12 is connected to the second adapter end 22, each first wire 231 is electrically connected with the corresponding output port 121 and further electrically connected with the corresponding connection port 112 due to the one-to-one correspondence between the output ports 121 and the connection ports 112, forming a closed circuit. At this time, the light emitting element 111 in the closed circuit emits light beams of corresponding peak wavelength which can be recognized by the monitor 30. In this way, it is possible to selectively electrically connect the specified light emitting element 111 to achieve the adaptation of the oximetry sensor 10 to the target monitor 30.

As shown in FIGS. 1-2, the oximetry sensor 10 further includes a first cable 13, where the first cable 13 has N+1 second wires 131. The second wires 131 connect each connection port 112 with the corresponding output port 121, respectively. Specifically, based on the provision of the second wires 131, each first wire 231 can be electrically connected to the corresponding connection ports 112 when the second adaptation end 22 is connected to the output end 12 to form a closed circuit. The light emitting element 111 between the two adjacent second wires 131 in the closed circuit is excited to emit light beams with a specific peak wavelength which can be recognized by the monitor 30.

As shown in FIG. 1, the first wires 231 are the same as the input ports of the target monitor 30 in number. The first adapter end 21 has a plurality of first adapter ports 211, and the first adapter ports 211 are the same as the first wires 231 in number. In an embodiment, the first adapter end 21 of the adapter 20 is a connector customized for the specific monitor 30. Since the input ports of the target monitor 30 are the same as the first wires 231 and the first adapter ports 211 in number, the first adapter ports 211 are electrically connected with the input ports of the target monitor 30 in a one-to-one correspondence when the first adapter end 21 is connected to the monitor 30, and further, the first wires 231 are electrically connected with the input ports of the target monitor 30 in a one-to-one correspondence, completing the adaptation between the first adapter end 21 and the monitor 30.

Figure 4:
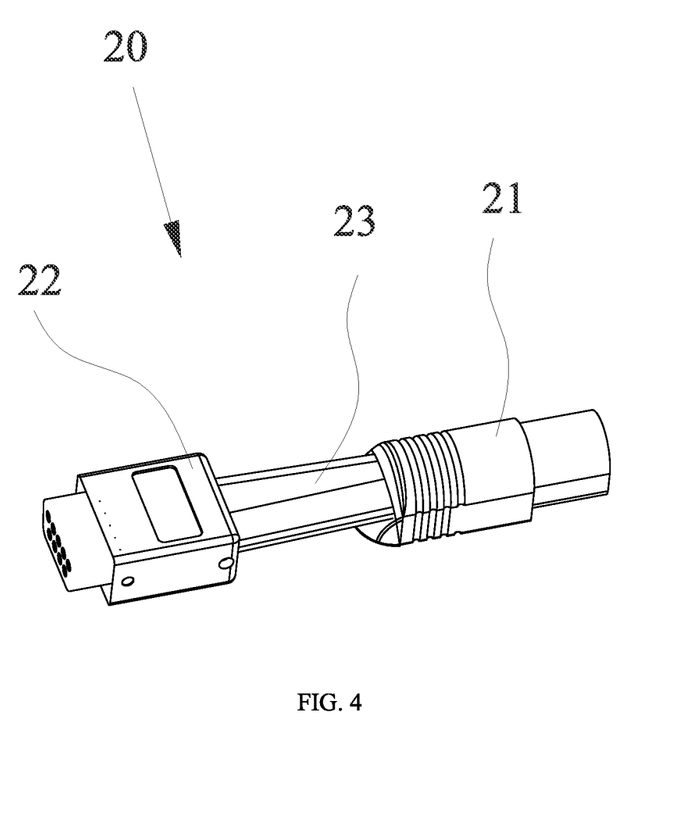
FIG. 4 schematically depicts the structure of the adapter according to another embodiment of the present invention.

As shown in FIGS. 1, 3 and 4, the first wires 231 can be packaged together in a rubber sheath to form a second cable 23, so as to make it more convenient for use.

As shown in FIG. 1, the second adapter end 22 has a plurality of second adapter ports 221, where the second adapter ports 221 are the same as the output ports 121 in number. Specifically, the adapter 20 connected to any monitor 30 has a second adapter end 22 adapting to the output end 12 of the oximetry sensor 10 in structure. The second adapter ports 221) are electrically connected with the corresponding output ports 121 through the first wires 231, controlling a specific light emitting element 111 to emit light.

In an embodiment, the first adapter end 21 is configured to connect with the input ports of the target monitor 30 or to connect with an external adapter connected to the input ports of the target monitor 30. Specifically, the adapter 20 is an electrical connector for adaptation, which plays a role in connecting the circuit set on the target monitor 30 for recognizing specific light combination to the detection end 11 of the oximetry sensor 10 to excite the corresponding light emitting elements 111 to emit the specific light combination, rendering the oximetry sensor 10 compatible with various monitors 30. The adapter 20 is connected between the oximetry sensor 10 and the input end of the monitor 30 to selectively and electrically connect the light emitting element 111 whose peak wavelength is compatible with the monitor 30, enabling the oximetry sensor 11 to adapt to the monitor 30. In an embodiment, the adapter 20 is connected between the oximetry sensor 10 and an OEM adapter to selectively and electrically connect the light emitting element 111 whose peak wavelength is compatible with the monitor 30. Moreover, the adapter 20 can also adapt to the port of the OEM adapter and then connect to the monitor 30 through the OEM adapter, enabling the oximetry sensor 10 to adapt to the monitor 30.

In an embodiment, the light emitting elements 111 are at least two red light emitting tubes and at least one infrared light emitting tube, where the at least two red light emitting tubes are connected in series to form a first series circuit, and the at least one infrared light emitting tube is connected in series to form a second series circuit. The first series circuit is connected in series with the second series circuit. Specifically, the light emitting elements 111 can be combined to form multiple light combinations to enable the oximetry sensor 10 to be compatible with various monitors 30 through the adapter 20.

For example, in this case that a light combination recognized by monitor A is Ra (peak wavelength of red light) and IRa (peak wavelength of infrared light), a light combination recognized by monitor B is Rb and IRb, and a light combination recognized by monitor C is Ra and IRb, a light emitting element 111 consisting of two red light emitting tubes and two infrared light emitting tubes is selected to enable the oximetry sensor 10 to be compatible with the above three types of monitors, where the peak wavelengths of the two red light emitting tubes are Ra and Rb, respectively, and the peak wavelengths of the two infrared light emitting tubes are IRa and IRb, respectively. The two red light emitting tubes are connected in series to form the first series circuit, and the two infrared light emitting tubes are connected in series to form the second series circuit. The first series circuit is connected with the second series circuit in series, and five connection ports 112 (P1, P2, P3, P4 and P5) are provided. The five connection ports 112 are connected with five output ports 121 through five second wires 131, respectively. For a given monitor, it is only required to connect the corresponding connection ports 112 at the detection end 11 to allow the corresponding light emitting element 111 to emit the light of specific peak wavelength which can be recognized by the given monitor. In the actual application, it is feasible to accordingly select a peak wavelength according to the monitor 30 required to be used, which can ensure the measurement error of the oximetry sensor 10 to be within ±2%.

In an embodiment, the light emitting elements 111 are at least one red light emitting tube and at least two infrared light emitting tubes, where the at least one red light emitting tube is connected in series to form a first series circuit, and the at least two infrared light emitting tubes are connected in series to form a second series circuit. The first series circuit is connected in series with the second series circuit. Specifically, in order to enable the oximetry sensor 10 to be compatible with the above three types of monitors 30, one red light emitting tube and two infrared light emitting tubes are employed as the light emitting elements 111, where the peak wavelength of the red light emitting tube is a median value in a range from the upper limit of Ra to the lower limit of Rb, and the upper limit of Ra is greater than the lower limit of Rb. The peak wavelengths of the two infrared light emitting tubes are IRa and IRb, respectively, and thus it is possible to replace the two red light emitting tubes required in the practical application with one red light emitting tube. The two infrared light emitting tubes are connected in series to form the series circuit, which is further connected with the one red light emitting tube in series. Four connection ports 112 are provided at the detection end 11. The four connection ports 112 are connected to the four output ports 121 through four second wires 131 in the first cable 13, respectively. Compared to the method mentioned above, this method has a relatively larger measurement error (within ±3%) in the practical application, but it can still meet the clinical requirements. Moreover, this method can significantly lower the production cost of the oximetry sensor 10.

In an embodiment, the detection end 11 further includes a circuit board, to which the red light emitting tubes and the infrared light emitting tubes are welded. Specifically, the red light emitting tubes and the infrared light emitting tubes are all welded to the same circuit board to form a light emitting chip, which not only simplifies the installation and manufacturing process, but also lowers the production cost.

In an embodiment, the detection end 11 further includes a first circuit board and a second circuit board. The red light emitting tubes are welded to the first circuit board, and the infrared light emitting tubes are welded to the second circuit board. Specifically, each red light emitting tube is welded to the same first circuit board to form a first chip, and each infrared light emitting tube is welded to the same second circuit board to form a second chip. The first and second chips are provided on the detection end 11, respectively. The red light emitting tubes and the infrared light emitting tubes are independently controlled for the light emitting.

In an embodiment, the detection end 11 further includes a first circuit board and a second circuit board, where one first circuit board is only welded with one red light emitting tube, and one second circuit board is only welded with one infrared light emitting tube. Specifically, each first circuit board is welded with a single red light emitting tube to form a first chip, and each second circuit board is welded with a single infrared light emitting tube to form a second chip, so that more light combinations can be obtained through permutation and combination of the red light emitting tubes and the infrared light emitting tubes, which is beneficial to improving the adaptation range of the oximetry sensor 10.

In an embodiment, the light emitting elements 111 are light emitting diode (LED) lights. The LED light is easy to control, and can emit the light of the target peak wavelength as required, which is conducive to the adaptation of the oximetry sensor 10 to the monitor 30.

Referring to FIGS. 1-2, an oximetry sensor 10 is also provided, which includes a detection end 11 and an output end 12. The detection end 11 includes a photodetector and a plurality of light emitting elements 111 capable of independently emitting light beams of different peak wavelengths. The light emitting elements 111 are connected in series. The output end 12 has a plurality of output ports 121. Two adjacent output ports 121 are electrically connected to two sides of the corresponding light emitting element 111, respectively. The output ports 121 are configured for electrical connection with an adapter of a monitor 30.

In the oximetry sensor 10 of the invention, due to the provision of multiple light emitting elements 111 capable of independently emitting light at the detection end 11, it is possible to selectively control the light emission of each light emitting element 111 as required, exciting the light combination corresponding to the specific monitor 30 to achieve the adaptation to different monitors 30. Given the above, the oximetry sensor 10 of the invention has desirable adaptation range and simple operation. When it is required to use a different monitor 30, it is only required to disconnect the output end 12 of the oximetry sensor 10 from the second adapter end 22 of the adapter 20 and then connect the output end 12 to a second adapter end 22 of an adapter 20 adapting to the different monitor 30 without the need to repeatedly remove and place the detection end 11 of the oximetry sensor 10, simplifying the operation and reducing the consumption of medical supplies.

In an embodiment, there are N light emitting elements 111, and N is greater than or equal to 3. The N light emitting elements 111 are connected in series, and N+1 connection ports 112 are provided. The two adjacent connection ports 112 are located at two sides of the corresponding light emitting element 111, respectively. The output end 12 has N+1 output ports 121 in one-to-one correspondence to the connection ports 112. Each connection port 112 is electrically connected with the corresponding output port 121. Specifically, when the output end 12 is connected to the second adapter end 22, each first wire (231) is electrically connected with the corresponding output port 121 and further electrically connected with the corresponding connection port 112 due to the one-to-one correspondence between the output ports 121 and the connection ports 112, forming a closed circuit. At this time, the light emitting element 111 in the closed circuit emits light beams of corresponding peak wavelength which can be recognized by the monitor 30. In this way, it is possible to selectively electrically connect the specified light emitting element 111 to form a light combination with a peak wavelength corresponding to the target monitor 30 achieve the adaptation of the oximetry sensor 10 to the target monitor 30.

As shown in FIGS. 1-2, the oximetry sensor 10 further includes a first cable 13, where the first cable 13 has N+1 second wires 131. The second wires 131 connect each connection port 112 with the corresponding output port 121, respectively. Specifically, based on the provision of the second wires 131, each first wire 231 can be electrically connected to the corresponding connection port 112 to form a closed circuit when the second adapter end 22 is connected to the output end 12. The light emitting element 111 between the two adjacent second wires 131 in the closed circuit is excited to emit light beams with a specific peak wavelength which can be recognized by the monitor 30.

In an embodiment, the light emitting elements 111 are at least two red light emitting tubes and at least one infrared light emitting tube, where the at least two red light emitting tubes are connected in series to form a first series circuit, and the at least one infrared light emitting tube is connected in series to form a second series circuit. The first series circuit is connected in series with the second series circuit. Specifically, the light emitting elements 111 can be combined to form multiple light combinations to enable the oximetry sensor 10 to be compatible with various monitors 30 through the adapter 20.

For example, in this case that a light combination recognized by monitor A is Ra (peak wavelength of red light) and IRa (peak wavelength of infrared light), a light combination recognized by monitor B is Rb and IRb, and a light combination recognized by monitor C is Ra and IRb, two red light emitting tubes and two infrared light emitting tubes are selected as the light emitting elements 111 to enable the oximetry sensor 10 to be compatible with the above three types of monitors, where the peak wavelengths of the two red light emitting tubes are Ra and Rb, respectively, and the peak wavelengths of the two infrared light emitting tubes are IRa and IRb, respectively. The two red light emitting tubes are connected in series to form the first series circuit, and the two infrared light emitting tubes are connected in series to form the second series circuit. The first series circuit is connected with the second series circuit in series to form five connection ports 112 (P1, P2, P3, P4 and P5). The five connection ports 112 are connected with five output ports 121 through five second wires 131, respectively. For a given monitor 30, it is only required to electrically connect the corresponding connection ports 112 at the detection end 11 to allow the corresponding light emitting element 111 to emit the light of specific peak wavelength which can be recognized by the given monitor. In the actual application, it is feasible to accordingly select a peak wavelength according to the monitor 30 required to be used, which can ensure the measurement error of the oximetry sensor 10 to be within ±2%.

In an embodiment, the light emitting elements 111 can be at least one red light emitting tube and at least two infrared light emitting tubes, where the at least one red light emitting tube is connected in series to form a first series circuit, and the at least two infrared light emitting tubes are connected in series to form a second series circuit. The first series circuit is connected in series with the second series circuit. Specifically, in order to enable the oximetry sensor 10 to be compatible with the above three types of monitors 30, one red light emitting tube and two infrared light emitting tubes are used as the light emitting elements 111, where the peak wavelength of the red light emitting tube is a median value in a range from the upper limit of Ra to the lower limit of Rb, and the upper limit of Ra is greater than the lower limit of Rb. The peak wavelengths of the two infrared light emitting tubes are IRa and IRb, respectively, and thus it is possible to replace the two red light emitting tubes required in the practical application with one red light emitting tube. The two infrared light emitting tubes are connected in series to form the series circuit, which is further connected with the one red light emitting tube in series. Four connection ports 112 are provided at the detection end 11. The four connection ports 112 are connected to the four output ports 121 through four second wires 131 in the first cable 13, respectively. Compared to the method mentioned above, this method has a relatively larger measurement error (within ±3%) in the practical application, but it can still meet the clinical requirements. Moreover, this method can significantly lower the production cost of the oximetry sensor 10.

In an embodiment, the detection end 11 further includes a circuit board, to which the red light emitting tubes and the infrared light emitting tubes are welded. Specifically, the red light emitting tubes and the infrared light emitting tubes are all welded to the same circuit board to form a light emitting chip, which not only simplifies the installation and manufacturing process, but also lowers the production cost.

In an embodiment, the detection end 11 further includes a first circuit board and a second circuit board. The red light emitting tubes are welded to the first circuit board, and the infrared light emitting tubes are welded to the second circuit board. Specifically, each red light emitting tube is welded to the same first circuit board to form a first chip, and each infrared light emitting tube is welded to the same second circuit board to form a second chip. The first and second chips are provided on the detection end 11, respectively. The red light emitting tubes and the infrared light emitting tubes are independently controlled for the light emitting.

In an embodiment, the detection end 11 further includes a first circuit board and a second circuit board, where one first circuit board is only welded with one red light emitting tube, and one second circuit board is only welded with one infrared light emitting tube. Specifically, each first circuit board is welded with a single red light emitting tube to form a first chip, and each second circuit board is welded with a single infrared light emitting tube to form a second chip, so that more light combinations can be obtained through permutation and combination of the red light emitting tubes and the infrared light emitting tubes, which is beneficial to improving the adaptation range of the oximetry sensor 10.

In an embodiment, the light emitting elements 111 are light emitting diode (LED) lights. The LED light is easy to control, and can emit the light of the target peak wavelength as required, which is conducive to the adaptation of the oximetry sensor 10 to the monitor 30.

Figure 5:
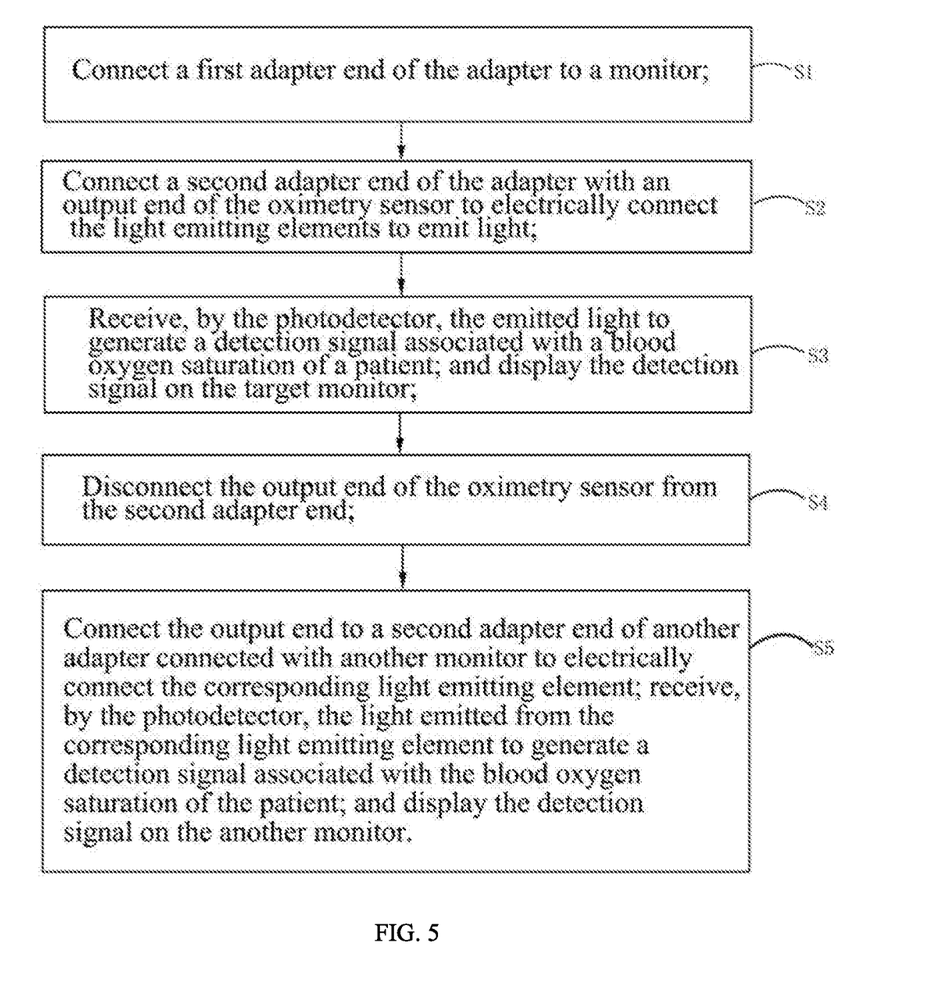
FIG. 5 is a flow chart showing an operating method of the oximetry probe according to an embodiment of the present invention.

As illustrated in FIG. 5, this application further provides a method of operating the above oximetry probe, which is specifically described as follows.

(1) The first adapter end 21 is connected to the target monitor 30 to allow one end of each first wire 231 to be electrically connected with the corresponding input port of the target monitor 30.

(2) The second adapter end 22 is connected with the output end 12 to allow the other end of each first wire 231 to be electrically connected with the corresponding output port 121 to form a closed circuit to enable the light emitting element 111 between the two adjacent output ports 121 in the closed circuit to emit light.

(3) The emitted light is received by the photodetector to form a detection signal associated with a blood oxygen saturation of a patient, which is then displayed on the target monitor 30.

(4) When it is required to use another monitor for blood oxygen monitoring, the output end 12 is disconnected from the second adapter end 22.

(5) The output end 12 is connected to a second adapter end 22 of another adapter 20 connected with the another monitor to enable the electric connection of the corresponding light emitting element 111. The light emitted from the corresponding light emitting element 111 is received by the photodetector to form a detection signal associated with the blood oxygen saturation of the patient, which is then displayed on the another monitor.

In the operating method, an adapter 20 adapting to the target monitor 30 is connected to the target monitor 30 in advance, and then a second adapter end 22 of the adapter 20 is connected to the output end 12 of the sensor 10 to selectively connect specific light emitting elements 111 from which the emitted light can be recognized by the target monitor 30, achieving the adaptation of the sensor 10 to the monitor 30. Therefore, when it is required to use a different monitor 30, it is only required to disconnect the output end 12 of the sensor 10 from the second adapter end 22 of the adapter 20 and then connect the output end 22 of the sensor 10 to a second adaptation end of an adapter adapting to the different monitor without the need to repeatedly remove and place the detection end 11 of the sensor 10, simplifying the operation and reducing the workload of the medical staff and the consumption of medical supplies.

Described above are merely preferred embodiments of the invention, which are not intended to limit the invention. Any modification, replacement and change made by those skilled in the art without departing from the spirit of the invention should still fall within the scope of the invention.

What is claimed is:

1. An oximetry probe, comprising:
an oximetry sensor; and
an adapter;
wherein the oximetry sensor comprises a detection end and an output end; the detection end comprises a photodetector and a plurality of light emitting elements capable of independently emitting light beams of different peak wavelengths; the light emitting elements are connected in series; the output end has a plurality of output ports; two adjacent output ports are electrically connected to two sides of the corresponding light emitting element, respectively;
the adapter has a first adapter end and a second adapter end; the first adapter end is configured to adapt to an input end of a target monitor; the second adapter end is configured to adapt to the output end of the oximetry sensor; a plurality of first wires are provided between the second adapter end and the first adapter end; the first adapter end is electrically connected with the input end of the target monitor to allow one end of each first wire to be electrically connected with a corresponding input port at the input end of the target monitor; the output ports are greater than the first wires in number; when the second adapter end is connected to the output end, the other end of each first wire is electrically connected with the corresponding output port to form a closed circuit, so as to enable the light emitting element between the two adjacent output ports in the closed circuit to emit light, and the emitted light is received by the photodetector to generate a detection signal associated with a blood oxygen saturation of a patient which is displayed on the target monitor.

2. The oximetry probe of claim 1, wherein there are N light emitting elements, and N is greater than or equal to 3; the N light emitting elements are connected in series; N+1 connection ports are provided at the detection end of the oximetry sensor; the two adjacent connection ports are located at two sides of the corresponding light emitting element, respectively; the output end of the oximetry sensor has N+1 output ports in one-to-one correspondence to the N+1 connection ports; and each connection port is electrically connected with the corresponding output port of the output end.

3. The oximetry probe of claim 2, wherein the oximetry sensor further comprises a cable; the cable has N+1 second wires; and the second wires connect each connection port with the corresponding output port, respectively.

4. The oximetry probe of claim 1, wherein the first wires are the same as input ports of the target monitor in number; the first adapter end has a plurality of first adapter ports; and the first adapter ports are the same as the first wires in number.

5. The oximetry probe of claim 4, wherein the second adapter end of the adapter has a plurality of second adapter ports; and the second adapter ports are the same as the output ports of the output end in number.

6. The oximetry probe of claim 1, wherein the first adapter end is configured to connect with the input end of the target monitor or to connect with an external adapter connected to the input end of the target monitor.

7. The oximetry probe of claim 1, wherein the light emitting elements comprise at least two red light emitting diodes and at least one infrared light emitting diode; the at least two red light emitting diodes are connected in series to form a first series circuit; the at least one infrared light emitting diode is connected in series to form a second series circuit; the first series circuit is connected in series with the second series circuit; or the light emitting elements comprise at least one red light emitting diode and at least two infrared light emitting diodes; the at least one red light emitting diode is connected in series to form a first series circuit; the at least two infrared light emitting diodes are connected in series to form a second series circuit; the first series circuit is connected in series with the second series circuit.

8. The oximetry probe of claim 7, wherein the detection end further comprises a circuit board; and the at least two red light emitting diodes and the at least one infrared light emitting diode are welded to the circuit board; or the at least one red light emitting diode and the at least two infrared light emitting diodes are welded to the circuit board.

9. The oximetry probe of claim 7, wherein the detection end further comprises a first circuit board and a second circuit board; and the at least two red light emitting diodes are welded to the first circuit board and the at least one infrared light emitting diode is welded to the second circuit board; or the at least one red light emitting diode is welded to the first circuit board and the at least two infrared light emitting diodes are welded to the second circuit board.

10. The oximetry probe of claim 7, wherein the detection end further comprises at least two first circuit boards and at least one second circuit board; the at least two red light emitting diodes are welded to the at least two first circuit boards in one-to-one correspondence; the at least one infrared light emitting diode is welded to the at least one second circuit board in one-to-one correspondence; or the detection end further comprises at least one first circuit board and at least two second circuit boards; the at least one red light emitting diode is welded to the at least one first circuit board in one-to-one correspondence; the at least two infrared light emitting diodes are welded to the at least two second circuit boards in one-to-one correspondence.

11. The oximetry probe of claim 1, wherein the light emitting elements are light emitting diode (LED) lights.

12. A method of operating the oximetry probe of claim 1, comprising:
(1) connecting the first adapter end to the target monitor to allow one end of each first wire to be electrically connected with the corresponding input port of the target monitor;
(2) connecting the second adapter end with the output end to allow the other end of each first wire to be electrically connected with the corresponding output port to form a closed circuit to enable the light emitting element between the two adjacent output ports in the closed circuit to emit light;
(3) receiving, by the photodetector, the emitted light to generate a detection signal associated with a blood oxygen saturation of a patient; and displaying the detection signal on the target monitor;
(4) when it is required to replace the target monitor with another monitor for blood oxygen monitoring, disconnecting the output end from the second adapter end of the adapter; and
(5) connecting the output end to a second adapter end of another adapter connected with the another monitor to enable the electric connection of the corresponding light emitting element; receiving, by the photodetector, the light emitted from the corresponding light emitting element to generate a detection signal associated with the blood oxygen saturation of the patient; and displaying the detection signal on the another monitor.

13. An oximetry sensor, comprising:
a detection end; and
an output end;
wherein the detection end comprises a photodetector and a plurality of light emitting elements capable of independently emitting light beams of different peak wavelengths; the light emitting elements are connected in series; the output end has a plurality of output ports; two adjacent output ports are electrically connected to two sides of the corresponding light emitting element, respectively; and the output ports are used for electrical connection with an adapter of a monitor; and there are N light emitting elements, and N is greater than or equal to 3; the N light emitting elements are connected in series; N+1 connection ports are provided at the detection end of the oximetry sensor; the two adjacent connection ports are located at two sides of the corresponding light emitting element, respectively; the output end has N+1 output ports in one-to-one correspondence to the connection ports; and each connection port is electrically connected with the corresponding output port.

14. The oximetry sensor of claim 13, further comprising:
a cable;
wherein the cable has N+1 wires; and the wires connect each connection port with the corresponding output port, respectively.

15. The oximetry sensor of claim 13, wherein the light emitting elements comprise at least two red light emitting diodes and at least one infrared light emitting diode; the at least two red light emitting diodes are connected in series to form a first series circuit; the at least one infrared light emitting diode is connected in series to form a second series circuit; the first series circuit is connected in series with the second series circuit; or the light emitting elements comprise at least one red light emitting diode and at least two infrared light emitting diodes; the at least one red light emitting diode is connected in series to form a first series circuit; the at least two infrared light emitting diodes are connected in series to form a second series circuit; the first series circuit is connected in series with the second series circuit.

16. The oximetry sensor of claim 15, wherein the detection end further comprises a circuit board; and the at least two red light emitting diodes and the at least one infrared light emitting diode are welded to the circuit board; or the at least one red light emitting diode and the at least two infrared light emitting diodes are welded to the circuit board.

17. The oximetry sensor of claim 15, wherein the detection end further comprises a first circuit board and a second circuit board; and the at least two red light emitting diodes are welded to the first circuit board and the at least one infrared light emitting diode is welded to the second circuit board; or the at least one red light emitting diode is welded to the first circuit board and the at least two infrared light emitting diodes are welded to the second circuit board.

18. The oximetry sensor of claim 15, wherein the detection end further comprises at least two first circuit boards and at least one second circuit board; the at least two red light emitting diodes are welded to the at least two first circuit boards in one-to-one correspondence; the at least one infrared light emitting diode is welded to the at least one second circuit board in one-to-one correspondence; or the detection end further comprises at least one first circuit board and at least two second circuit boards; the at least one red light emitting diode is welded to the at least one first circuit board in one-to-one correspondence; the at least two infrared light emitting diodes are welded to the at least two second circuit boards in one-to-one correspondence.

19. The oximetry sensor of claim 13, wherein the light emitting elements are light emitting diode (LED) lights.

\* \* \* \* \*